United States Patent [19]
Warthen

[11] Patent Number: 4,845,851
[45] Date of Patent: Jul. 11, 1989

[54] SYNTHETIC SUTURE CUTTING DEVICE

[75] Inventor: William P. Warthen, Spartanburg, S.C.

[73] Assignee: Milliken Research Corporation, Spartanburg, S.C.

[21] Appl. No.: 130,587

[22] Filed: Dec. 9, 1987

[51] Int. Cl.⁴ .................... B26F 3/08; B32B 31/18
[52] U.S. Cl. ................................ 30/140; 156/251; 156/515; 289/18.1
[58] Field of Search ........................ 289/2, 17, 18.1; 156/251, 433, 502, 515; 30/140

[56] References Cited
U.S. PATENT DOCUMENTS 3,772,127  11/1973  James ............................ 156/502
4,030,743   6/1977  Warthen ........................ 289/18.1
4,106,973   8/1978  Wright ......................... 156/515 X
4,285,753   8/1981  Warthen ........................ 156/251

Primary Examiner—Frank T. Yost
Assistant Examiner—Michael D. Folkerts
Attorney, Agent, or Firm—Terry T. Moyer; H. William Petry

[57] ABSTRACT

A device is provided for severing the tails of a knot formed in sutures of a wide variety of cross-sectional dimensions which includes a housing, an electrical heating element forming at least a portion of a notch, guide means operably associated with the heating element and the housing, the guide means functioning to bring the tails of the knot into contact with the heating element and meams for electrically supplying power to the heating element.

6 Claims, 3 Drawing Sheets

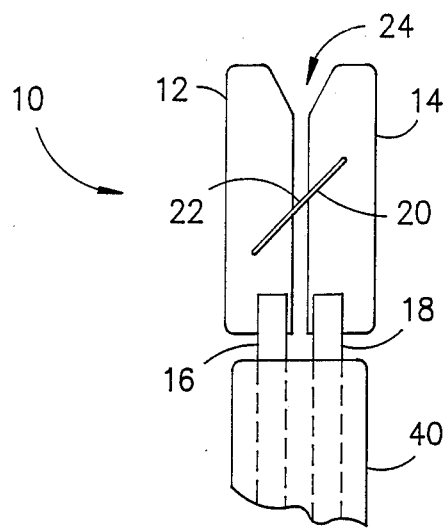
FIG. -1-
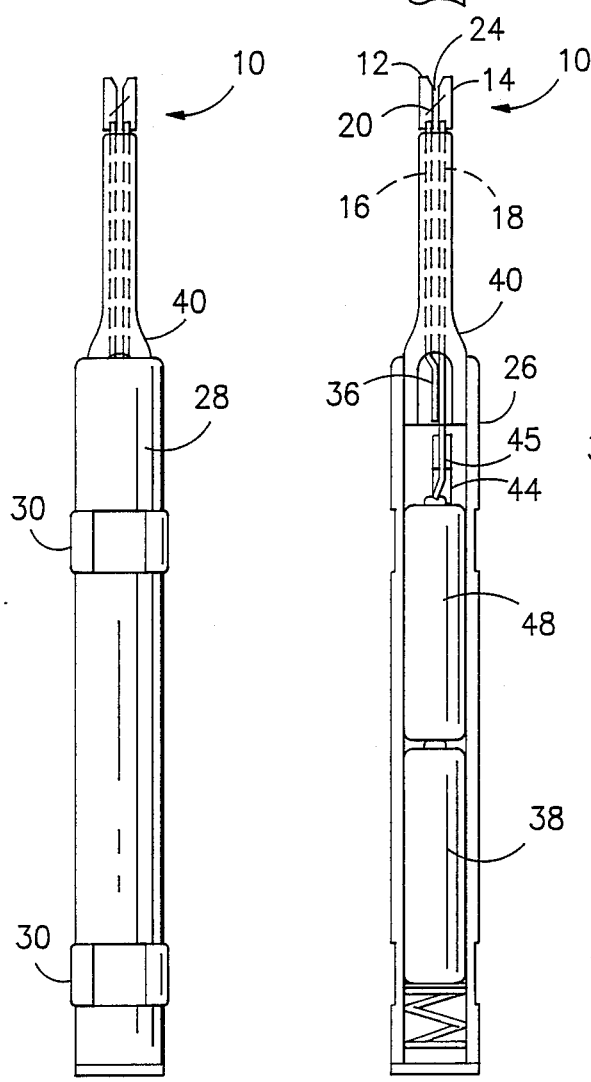
FIG. -2A- FIG. -2B-
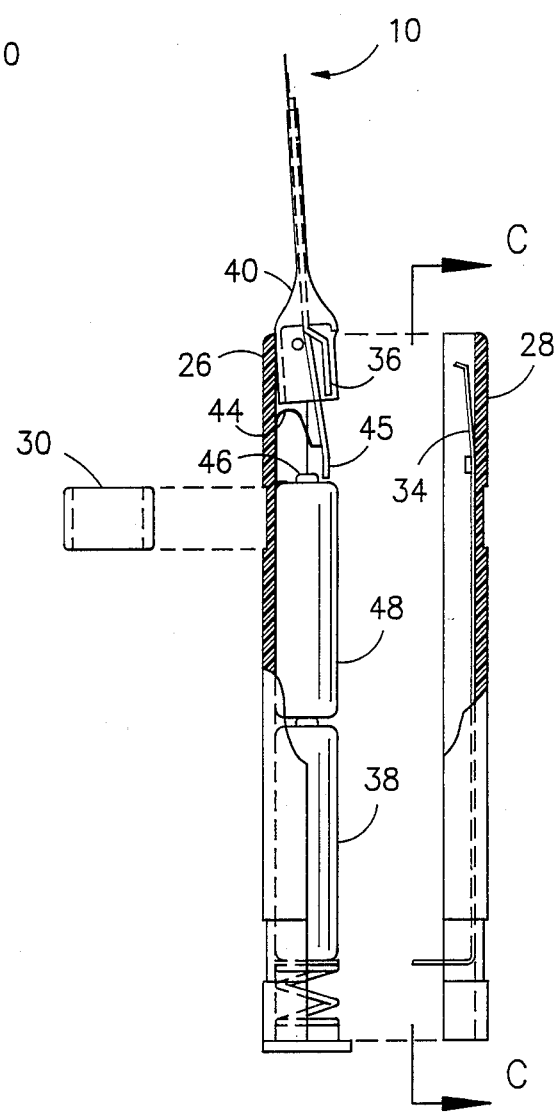
FIG. -2D-

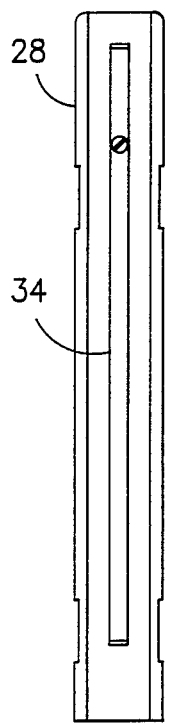
FIG. -2C-
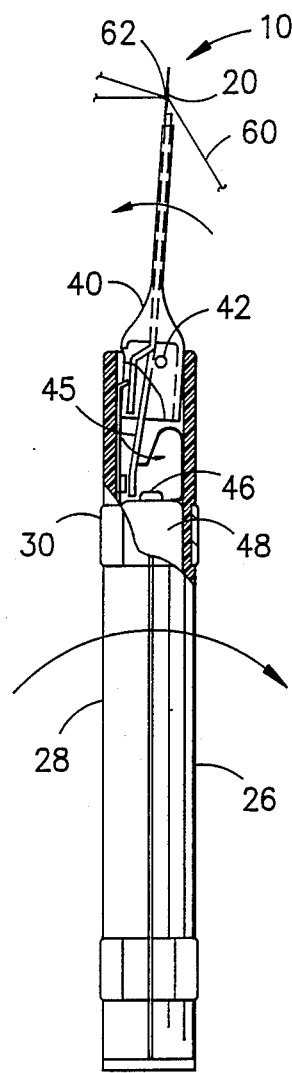
FIG. -3-
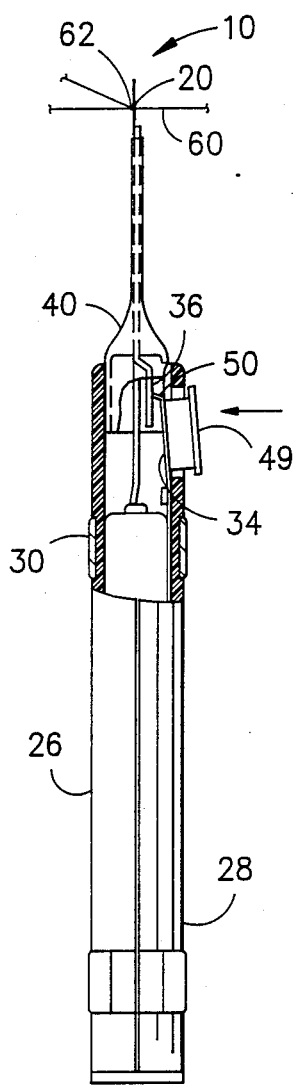
FIG. -4-
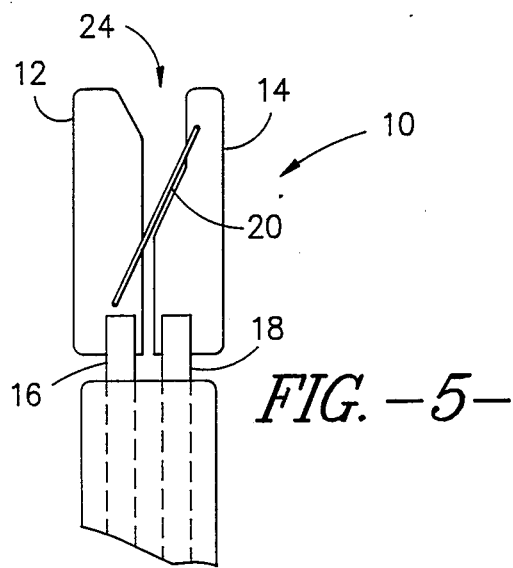
FIG. -5-
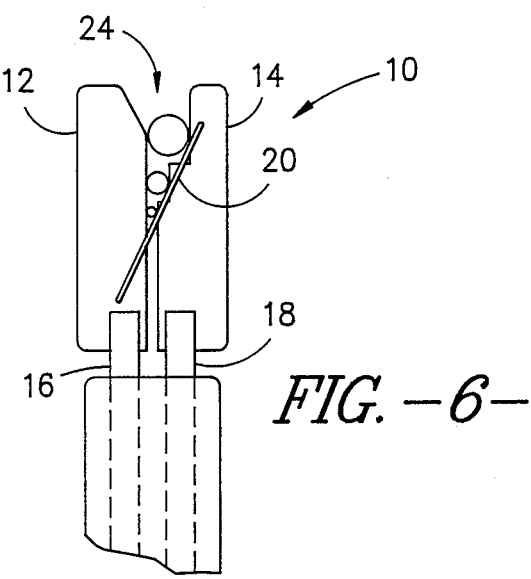
FIG. -6-

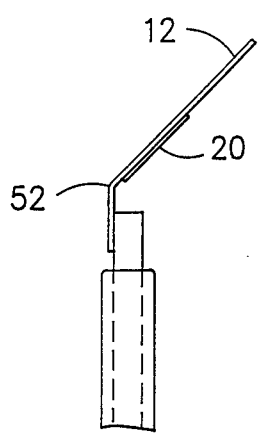
FIG.—7—
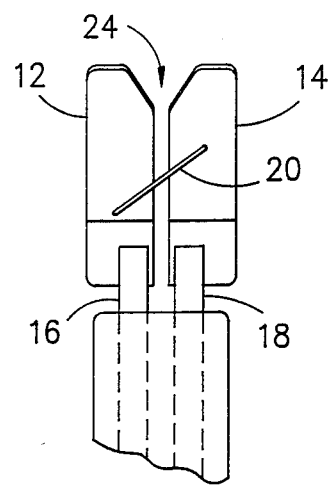
FIG.—8—
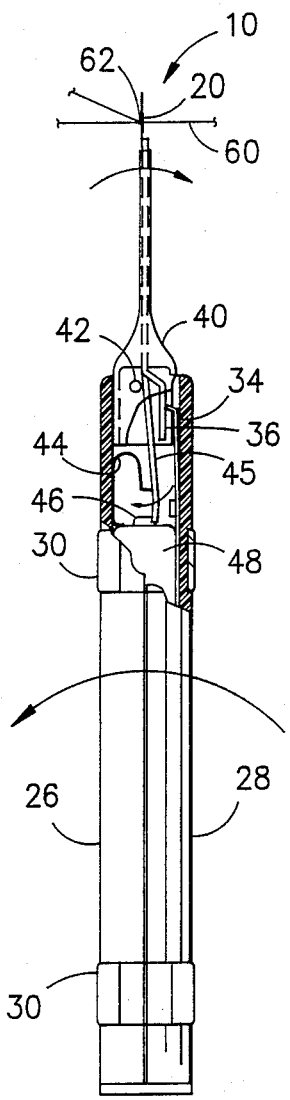
FIG.—9—
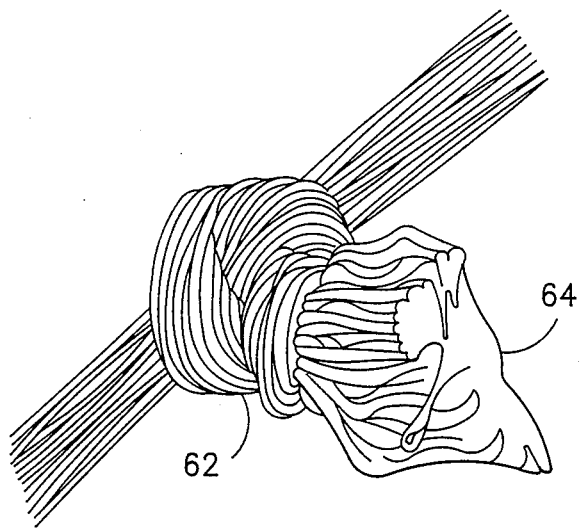
FIG.—10—

SYNTHETIC SUTURE CUTTING DEVICE

The present invention relates to a device for cutting sutures and other yarns and threads. More particularly, the present invention relates to a device for making slip resistant knots in synthetic sutures and other synthetic yarns having a wide range of cross-sectional dimensions.

During surgical procedures it is important that any knots that may be tied by the surgeon or his assistants to secure sutures together do not slip, especially where those knots may be tied inside the body. Unfortunately, however, many surgical suture constructions are such that slippage of a particular knot that may be tied may occur. Thus the surgeon must take great pains to tie elaborate knots consisting of many "throws" to make certain that the knots he ties will not slip. The tieing of such knots requires considerable skill and practice (and is therefore somewhat subject to human error) and may consume a considerable amount of time during a surgical procedure.

The device of the present invention, which involves heat cutting of the knot tails, provides means for achieving significantly improved knot security of sutures comprised of synthetic materials. This result may be achieved with less complex knot constructions, e.g., by means of fewer "trows", as compared to current practice which involves a manually constructed knot wherein the knot tails are cut with conventional scissors. Reduction of the number of throws may decrease the time required for wound closure.

Also, according to the present invention, the knot tails which may be achieved are usually substantially shorter than those normally occurring using conventional techniques. With fewer throws and shorter tails the amount of foreign suture material implanted in the tissue of the patient may be reduced, an advantage readily apparent to those skilled in the art.

The device of the present invention is relatively simple to use and in fact may be used to achieve non-slipping knots with a minimum of skill and practice, especially as contrasted to conventional procedures. The device of the present invention may, furthermore, be used on a wide variety of synthetic suture constructions and diameters without the need for adjustment or replacement of the cutting mechanism.

Pursuant to one or more embodiments of the present invention, the electrical power to the heating element which functions to sever the knot tails is automatically interrupted upon severance of the knot tails. Any possibility of overheating and injuring nearby tissue is thereby minimized or avoided.

According to the present invention a device is provided for severing the tails of a knot formed in sutures of a wide variety of cross-sectional dimensions. The device is comprised of a housing which may serve as a handle for the operator to grasp and may also house operating components such as a source of electrical power. A cutter head is mounted on the housing and it may be pivotally mounted thereon so as to form a switch to turn the power to the cutter head on and off as desired. The cutter head includes a guide and an electrical heating element. The guide functions to bring the knot tails into contact with the heating element. It may also function to separate or insulate the heating element from the knot to prevent or minimize degradation of the knot from heat generated by the heating element.

The heating element forms all or part of a notch, a generally V-shaped portion of the cutter head, that allows a wide variety of suture diameters to slide through it while the operator slides the cutter head down along the suture tails until the device comes into engagement with the knot. The notch is so designed, however, that while suture tails of a wide variety of cross-sections will easily slide through it, the knots formed in those sutures will not pass through the notch when the device is used properly. Thus when cutter head comes into engagement with the knot with the tails in the notch, power will be supplied to the heating element which will cause the tails to be severed from the knot. Power may then be disengaged by any of a wide variety of means as will be discussed herein.

When the suture or other thread or yarn is made from a thermoplastic material additional advantages may be observed. Thus the portion of the knot tails remaining after severance are generally somewhat swollen making it more difficult for them to pass back through the knot itself thereby preventing the knot from slipping.

In one embodiment the operator places the knot tails within the slot and moves the device towards the knot. When the device makes contact with and pushes against the knot the electrical circuit is closed connecting the source of power to the heater element. The heat generated by the heater element will sever the knot tails from the knot whereupon the operator will remove the device from the knot which results in disengagement of the power to the heater element.

In another embodiment, which is the preferred embodiment, the operator places the knot tails within the slot and moves the device towards the knot until it comes into contact with the knot. The operator then angles the knot tails downwardly and pulls the device in a general direction away from the knot while maintaining the position of the device relative to the knot. This procedure causes the electrical circuit to be closed connecting the source of power to the heater element. The heat generated by the heater element will sever the knot tails from the knot which frees the device from engagement with the knot and allows it to fall away from the knot whereupon the power to the heater head is automatically disengaged thus minimizing the possibility of damage to the knot or surrounding tissue by overheating.

According to yet another embodiment of the invention the device is simply brought into contact with the knot and power is manually supplied to the heater means by pressing a button. When the tails are severed the button is released and the power is disengaged.

As will be apparent to those skilled in the art the device may be reused many times if desired or, alternatively, the cost of manufacture of the device is such that it may be used for a single operation and then discarded.

Other object and advantages of the invention will become apparent by reference to the accompanying drawings, in which:

FIG. 1 is a frontal view of one embodiment of the new and improved cutter head of the device.

FIG. 2A is a side view of the assembled device.

FIG. 2B is a planar view of the device with the cover removed.

FIG. 2C is a view along line C shown in FIG. 2D.

FIG. 2D is a cutaway side view of the device.

FIG. 3 is a cutaway side view of an alternative embodiment of the invention showing the suture tailings in position for severing from the knot.

FIG. 4 is a cutaway view of the "push button" embodiment of the invention.

FIGS. 5-8 are views of alternative embodiments of the cutter head.

FIG. 9 is a side view of embodiment shown in FIGS. 2A-2D in a "power-on" position.

FIG. 10 shows a typical suture knot and tails after cutting.

Referring now to the drawings and in particular to FIG. 1, the cutter head 10 is illustrated having electrically conductive strips 12 and 14 mounted on electrically conductive members 16 and 18. A resistance heater element 20 made of nichrome or other suitable material interconnects the strips 12 and 14. Strips 12, 14 may have any desired shape and may be comprised of stiff wire. It is not essential that strips 12, 14 be electrically conductive so long as electricity is available to heater element 20. Alternatively, strips 12, 14 and conductive members 16, 18 may be combined into a single pair of elements. Resistance heater element 20 is mounted at a mounting angle relative to slot 24, as determined within slot 24, at, e.g., 22.. The slot 24 between conductive strips 12 and 14 is sufficiently wide, e.g. from about .01 to about .80 millimeters, preferably from about 0.40 to about 0.60 millimeters, to accommodate virtually all of the conventional synthetic surgical suture materials currently on the market. Excessive "play" of the sutures if they are substantially less in a cross-sectional dimension than the width of slot 24, is avoided by the nestling of the sutures in the notch formed by the heating element 20 and conductive member 12. When the head 10 is moved down towards a given knot with the suture tails within slot 24, the knot will not pass through the slot. When head 10 meets the knot, heating element 20 is activated, and the tails are severed from the knot. If desired, heater element 20 may be positioned relative to slot 24 at an angle whereby element 20 extends along a substantial length of slot 24. Referring now to FIGS. 2A-2D, the new and improved, synthetic suture cutter is housed in a plastic casing comprising mating casing members 26 and 28, held together in mating relationship by two plastic slip rings 30.

Mounted on the back of casing member 28 is electrical conductor 34, shown in FIG. 2C, which may be of berillium, copper, brass or other suitable conducting material and which forms the return path from contact surface 36 of conductive member 16 to the negative terminal of battery 38. Conductive members 16 and 18 are embedded in a plastic block 40 which is pivotally mounted at pivot point 42. Spring member 44, mounted on casing member 26, engages extension 45 of conductive member 18, holding it out of contact with the positive terminal 46 of battery 48. When head 10 engages a knot with the knot tails in slot 24, the pressure applied to head 10 causes head 10 to pivot about point 42, bringing extension 45 of conductive member 18 into contact with positive terminal 46 and completing the electrical circuit by which heater element 20 is connected to the power source comprised of batteries 48 and 38. This causes the heater element 20 to heat up, thereby severing the tails from the knot.

FIG. 3 represents the preferred embodiment of the invention wherein the resistance heater element 20 is actuated by pulling the cutter head 10 away from the knot 62, rather than by applying pressure in the direction of the knot 62. According to this embodiment, the tails 60 are angled downwardly such that when the cutter head 10 is moved away from the knot 62, the cutter head 10 will pivot around pivot point 42. This brings extension 45 into contact with the positive terminal 46 and completes the circuit, causing the heater element 20 to heat up and sever the tails of the knot. As can be seen, the embodiment shown in FIG. 3 may have certain advantages because, immediately upon severing of the tails 60 from the knot 62, the cutter head 10 will move away from the knot (and any surrounding body tissues). As a result extension 45 of conductive member 18 will be disengaged from positive terminal 46, interrupting the electric power and minimizing the possibility of any overheating of the knot or surrounding body tissues.

FIG. 4 illustrates another embodiment of the invention, wherein actuation of the heater 20 is caused by a pushbutton mechanism and the cutter head 10 is permanently and non-movably mounted in the casing. The heater element 20 is actuated manually by pushing button 49, which causes extension 50 of conductor 34 to come into contact with extension 36 of conductive member 16.

FIG. 5 shows an alternative embodiment of the invention wherein the shape of conductive plate 14 has been modified to conform essentially to the angle of heater element 20. This facilitates the accommodation of widely varying suture diameters but prevents the knot formed in those sutures from slipping through the aperture 24. In FIG. 6 the shape of conductive plate 14 has been modified to show a stepwise configuration such that the accommodation of sutures having widely divergent cross sectional dimensions may be accommodated. FIGS. 7 and 8 illustrate yet another embodiment of the invention wherein the conductive plates 12 and 14 have been angled, as shown at position 52, to facilitate the cutting of suture tails at hard to reach locations within a body cavity.

As noted above, it is desired to connect two ends of a synthetic surgical suture (generally a thermoplastic material) together so that the connecting point, normally a knot, will not slip. It is also desired to make the tail ends of the knot as short as possible to limit the amount of foreign material remaining in the body after the surgery. To accomplish this the tailing ends 60 of the knot 62 are placed between the conductive plates 12 and 14 in the aperture 24, as shown in FIGS. 9 and 10. Head 10 is then slid down along the tail ends until it comes into contact with knot 62. Electrical power may then be supplied to the resistance heater element 20 by any of the various actuation mechanisms described herein. When heater element 20 heats up, it will separate the suture knot tails 60 from the knot 62 and, as shown in FIG. 10, allow the individual filaments or fibers of the suture to swell up to form knot locking portion 64 preventing knot 62 from slipping.

Electrical power to the resistance heater then may be interrupted either manually according to one embodiment, or automatically according to alternative embodiments. When the power is interrupted automatically, according to a preferred embodiment, exposure of the knot and surrounding body tissue to needless overheating as a result of operator error which could result in degradation of knot strength and damage to body tissue may be avoided or minimized.

It is to be understood that while the device of the invention has been described with regard to synthetic surgical sutures and surgical procedures it may have applications in other fields such as, for instance, the textile fields for cutting, for instance, yarns and threads, especially those products made from thermoplastic raw materials.

Although the preferred embodiments of the present invention have been described in detail, it is contemplated that changes may be made without departing from the scope or spirit of the invention and it is desired that the invention only be limited by the scope of the claims.

I claim:

1. A device for severing the tails of a knot formed in sutures of a wide variety of cross sectional dimensions, comprising:
   (a) a housing;
   (b) a pair of spaced, opposed guides extending from said housing, said guides forming a slot having sufficient width to accommodate the largest cross sectional dimension of said sutures;
   (c) an electrical heating element positioned across said slot at an oblique angle forming a notch such that one side wall of said notch is formed from one of said guides and the other side wall of said notch is formed from said heating element; and
   (d) means for interruptibly supplying electrical power to said heating element.

2. The device of claim 1 wherein said oblique angle of said notch is from about 70 degrees to about 25 degrees.

3. The device of claim 1 wherein said electrical power is provided by a power source within said housing.

4. The device of claim 1 wherein said heating element and said guide means form a cutting head and wherein power is supplied to said heating element by the application of force to said cutting head in a direction away from said knot while said tails are in contact with said heating element.

5. The device of claim 4 wherein said power is automatically interrupted by the cessation of said force which occurs upon severance of said tails.

6. A device for severing the tails of a knot tied in a surgical suture, which comprises a housing; a source of electrical power in said housing; a pair of electrically conductive members mounted on said housing operably associated with said source of electrical power and spaced from one another forming a slot wherein the side wall of at least one of said electrically conductive members forming said slot is shaped in a descending stepwise manner to accommodate surgical sutures of varying cross sectional dimensions; a resistance heater means connected to both of said conductive members and mounted on said conductive members at a mounting angle forming a notch such that a wide range of suture diameters will pass through said slot and means operably associated with said source of electrical power and said electrically conductive members to supply electrical power to said heater means.

* * * * *